United States Patent [19]

Berg

[11] Patent Number: 4,909,907

[45] Date of Patent: * Mar. 20, 1990

[54] SEPARATION OF FORMIC ACID FROM ACETIC ACID BY EXTRACTIVE DISTILLATION WITH ACETYL SALICYLIC ACID

[75] Inventor: Lloyd Berg, Bozeman, Mont.

[73] Assignee: Hoechst Celanese Chemical Co., Pampa, Tex.

[*] Notice: The portion of the term of this patent subsequent to Sep. 8, 2004 has been disclaimed.

[21] Appl. No.: 298,872

[22] Filed: Jan. 17, 1989

Related U.S. Application Data

[63] Continuation-in-part of Ser. No. 98,082, Sep. 21, 1987, abandoned.

[51] Int. Cl.[4] .......................... B01D 3/40; C07C 53/02
[52] U.S. Cl. ........................................ 203/51; 203/56; 203/58; 203/60; 203/61; 203/62; 203/65; 562/608; 562/609
[58] Field of Search ....................... 203/51, 60, 61, 58, 203/62, 65, 56, 15, 16; 562/608, 609

[56] References Cited

U.S. PATENT DOCUMENTS

| | | | |
|---|---|---|---|
| 3,394,058 | 7/1968 | Hohenschutz | 203/15 |
| 3,437,566 | 4/1969 | Gasser et al. | 562/609 |
| 3,660,483 | 5/1972 | Hobbs et al. | 562/608 |
| 3,801,629 | 4/1974 | Aga et al. | 562/608 |
| 4,110,372 | 8/1978 | Hey et al. | 562/608 |
| 4,576,683 | 3/1986 | Cohen | 562/608 |
| 4,692,219 | 9/1987 | Berg | 203/51 |

FOREIGN PATENT DOCUMENTS

| | | | |
|---|---|---|---|
| 386907 | 10/1973 | U.S.S.R. | 562/609 |
| 445645 | 12/1974 | U.S.S.R. | 203/61 |

Primary Examiner—Wilbur Bascomb

[57] ABSTRACT

Formic acid cannot be easily removed from acetic acid by distillation because of the closeness of their vapor pressures. Formic acid can be readily removed from acetic acid by extractive distillation. Typical extractive distillation agents are acetyl salicylic acid and butyl benzoate; acetyl salicylic acid and ethylene carbonate.

2 Claims, No Drawings

SEPARATION OF FORMIC ACID FROM ACETIC ACID BY EXTRACTIVE DISTILLATION WITH ACETYL SALICYLIC ACID

This is a continuation in part of Appl. 07/098,082 filed Sept. 21, 1987, abandoned

FIELD OF THE INVENTION

This invention relates to a method for separating formic acid from acetic acid using certain higher boiling liquids as the agent in extractive distillation.

DESCRIPTION OF THE PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling compound. This usually requires that the extractive agent boil twenty Centigrade degrees or more above the lowest boiling component.

At the bottom of a continuous column, the less volatile components of the close boiling mixture and the extractive agent are continuously removed from the column. The usual methods of separation of these two components are the use of another rectification column, cooling and phase separation or solvent extraction.

Some of the manufacturing processes for producing mono carboxylic acids result in a product containing both formic acid and acetic acid. For example, the oxidation of n-butane yields a mixture of oxygen-containing organic compounds including formic and acetic acids as well as some water. Formic acid boils at 100.8° C. but in the presence of water, the maximum azeotrope boiling at 107.2° C. is formed. Acetic acid boils at 118.1° C. Thus an aqueous mixture of formic acid and acetic acid will be a mixture boiling in the rather narrow range 100°–118.1° C. The relative volatility of formic acid to acetic acid is about 1.15. The difficulty in separating formic acid from acetic acid by rectification can be shown by Table 1.

TABLE 1

Theoretical Plates Required To Effect Separation of 99% Purity

| Relative Volatility | Theoretical Plates |
|---|---|
| 1.15 | 92 |
| 1.3 | 35 |
| 1.7 | 17 |
| 2.0 | 13 |
| 2.2 | 11.5 |

Table 1 shows that to separate formic acid from acetic acid in 99% purity, 92 theoreical plates are required. If the relative volatility could be improved from the 1.15 value to 2, the theoretical plate requirement drops to 13.

Extractive distillation would be an attractive method of effecting the separation of formic acid from acetic acid if agents can be found that (1) will increase the relative volatility of formic acid to acetic acid and (2) are easy to recover from acetic acid, that is, form no azeotrope with acetic acid and boil sufficiently above acetic acid to make the separation by rectification possible with only a few theoretical plates.

Extractive distillation typically requires the addition of an equal amount to twice as much extractive agent as the formic acid - acetic acid on each plate of the rectification column. The extractive agent should be heated to about the same temperature as the plate into which it is introduced. Thus extractive distillation imposes an additional heat requirement on the column as well as somewhat larger plates. However this is less than the increase caused by the additional agents requires if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent be miscible with the acetic acid otherwise it will form a two-phase azeotrope with the acetic acid in the recovery column and some other method of separation will have to be employed.

One of the present methods of separating formic acid from acetic acid is the use of azeotropic distillation. Effective azeotrope formers are hydrocarbons boiling sufficiently lower than formic acid so that they will form a minimum azeotrope with formic acid but not with acetic acid. Benzene, b.p. =80° C., is currently the hydrocarbon in use.

OBJECTIVE OF THE INVENTION

The object of this invention is to provide a process or method of extractive distillation that will enhance the relative volatility of formic acid from acetic acid in their separation in a rectification column. It is further object of this invention to identify organic compounds which in addition to the above constraints, are stable, can be separated from acetic acid by rectification with relatively few theoretical plate and can be recycled to the extractive distillation column and reused with little decomposition.

SUMMARY OF THE INVENTION

The objects of the invention are provided by a process for separating formic acid from acetic acid which entails the use of acetyl salicylic acid, commonly called aspirin, mixed with certain high boiling organic compounds in an extractive distillation.

DETAILED DESCRIPTION OF THE INVENTION

I have discovered that mixtures containing acetyl salicylic acid, commonly called aspirin, and certain high boiling organic compounds will effectively enhance the relative volatility of formic acid to acetic acid and permit the separation of formic acid from acetic acid by rectification when employed as the agent in extractive distillation. Table 2 lists mixtures containing acetyl salicylic acid (aspirin) and certain high boiling organic compounds and the approximate proportions that I have found to be effective. The data in Table 2 was obtained in a vapor-liquid equilibrium still. In each case, the starting material was a mixture containing 40% water, 32% formic acid and 28% acetic acid. The ratios are the parts by weight of extractive agent per part of water - formic acid - acetic acid mixture. The relative voltilities are listed for each of the two ratios employed.

The compounds which are effective when used with aspirin are hexanoic acid, heptanoic acid, pelargonic acid, decanoic acid, neodecanoic acid, acetophenone, 2-hydroxyacetophenone, 4-hydroxyacetophenone, n-amyl acetate, methyl amyl acetate, butyl benzoate, ethyl benzoate, methyl benzoate, dipropylene glycol dibenzoate, methyl salicylate, cyclohexanone, 2-heptanone, diisobutyl ketone, isophorone, ethylene carbonate, propylene carbonate and octanoic acid. The relative volatilities shown in Table 2 correspond to the two different ratios investigated. For example, in Table 2, one part of aspirin plus one part of hexanoic acid mixed with one part of the water - formic acid - acetic acid mixture gives a relative volatility of 2.6; 6/5 parts of aspirin plus 6/5 parts of hexanoic acid give a relative volatility of 2.4. One-third part of aspirin plus ⅓ part of hexanoic acid plus ⅓ part of isophorone mixed with the water - formic acid - acetic acid mixyture gives a relative volatility of 2.1; with 2/5 parts, these three give a relative volatility of 2.3. With no agent present, the relative volatility of formic acid to acetic acid is 1.15.

A mixture of 50% aspirin, 50% heptanoic acid, listed in Table 2 and whose relative volatility had been determined in the vapor-liquid equilibrium still, was then evaluated in a glass perforated plate rectification column possessing 4.5 theoretical plates and the results listed in Table 3. The data in Table 3 was obtained in the following manner.

TABLE 2

Effective Extractive Distillation Agents

| Compounds | Ratios | | Relative Volatilities | |
|---|---|---|---|---|
| Acetyl salicylic acid (Aspirin), Hexanoic acid | $(1/2)^2$ | $(3/5)^2$ | 2.6 | 2.4 |
| Aspirin, Heptanoic acid | " | " | 2.2 | 2.1 |
| Aspirin, Pelargonic acid | " | " | 1.9 | 2.0 |
| Aspirin, Decanoic acid | " | " | 1.9 | 1.9 |
| Aspirin, Neodecanoic acid | " | " | 2.4 | 2.3 |
| Aspirin, Acetophenone | " | " | 2.2 | 2.0 |
| Aspirin, 2-Hydroxyacetophenone | " | " | 2.0 | 1.9 |
| Aspirin, 4-Hydroxacetophenon | " | " | 1.8 | 2.2 |
| Aspirin, n-Amyl acetate | " | " | 1.6 | 1.7 |
| Aspirin, Methyl amyl acetate | " | " | 2.1 | 1.7 |
| Aspirin, Butyl benzoate | " | " | 2.1 | 2.1 |
| Aspirin, Ethyl benzoate | " | " | 2.1 | 2.1 |
| Aspirin, Methyl benzoate | " | " | 2.2 | 2.4 |
| Aspirin, Dipropylene glycol dibenzoate | " | " | 2.0 | 1.7 |
| Aspirin, Methyl salicylate | " | " | 2.2 | 2.1 |
| Aspirin, Cyclohexanone | " | " | 2.2 | 2.4 |
| Aspirin, 2-Heptanone | " | " | 1.7 | 1.7 |
| Aspirin, Diisobutyl ketone | " | " | 2.2 | 2.4 |
| Aspirin, Isophorone | " | " | 2.0 | 1.6 |
| Aspirin, Ethylene carbonate | " | " | 2.4 | 2.5 |
| Aspirin, Hexanoic acid, Acetophenone | $(1/3)^3$ | $(2/5)^3$ | 1.8 | 1.5 |
| Aspirin, Hexanoic acid, 2-hydroxacetophenone | " | " | 2.5 | 2.2 |
| Aspirin, Hexanoic acid, 4-hydroxyacetophenone | " | " | 1.7 | 1.6 |
| Aspirin, Hexanoic acid, n-Amyl acetate | " | " | 2.3 | 1.9 |
| Aspirin, Hexanoic acid, Methyl amyl acetate | " | " | 1.9 | 1.9 |
| Aspirin, Hexanoic acid, Butyl benzoate | " | " | 1.5 | 1.9 |
| Aspirin, Hexanoic acid, Methyl salicylate | " | " | 2.3 | 2.0 |
| Aspirin, Hexanoic acid, Cyclohexanone | " | " | 2.0 | 1.9 |
| Aspirin, Hexanoic acid, 2-Heptanone | " | " | 1.7 | 1.8 |
| Aspirin, Hexanoic acid, Diisobutyl ketone | " | " | 1.6 | 2.2 |
| Aspirin, Hexanoic acid, Isophorone | " | " | 2.1 | 2.3 |
| Aspirin, Hexanoic acid, Ethylene carbonate | " | " | 1.5 | 1.6 |
| Aspirin, Hexanoic acid, Propylene carbonate | " | " | 1.5 | 1.4 |
| Aspirin, Heptanoic acid, 2-Hydroxacetophenone | " | " | 2.6 | 2.2 |
| Aspirin, Heptanoic acid, 4-Hydroxyacetophenone | " | " | 2.2 | 2.0 |
| Aspirin, Heptanoic acid, Methyl benzoate | " | " | 2.1 | 1.9 |
| Aspirin, Heptanoic acid, Cyclohexanone | " | " | 2.4 | 2.3 |
| Aspirin, Heptanoic acid, Isophorone | " | " | 2.2 | 2.3 |
| Aspirin, Heptanoic acid, Ethylene carbonate | " | " | 1.6 | 2.1 |
| Aspirin, Heptanoic acid, Propylene carbonate | " | " | 2.1 | 2.4 |
| Aspirin, Octanoic acid, Cyclohexanone | $(1/3)^3$ | $(2/5)^3$ | 1.7 | 1.7 |
| Aspirin, Octanoic acid, Ethylene carbonate | " | " | 1.4 | 1.4 |
| Aspirin, Octanoic acid, Propylene carbonate | " | " | 1.7 | 1.6 |
| Aspirin, Pelargonic acid, Acetophenone | " | " | 2.1 | 1.8 |
| Aspirin, Pelargonic acid, 2-Hydroxyacetophenone | " | " | 2.2 | 2.6 |
| Aspirin, Pelargonic acid, 4-Hydroxyacetophenone | " | " | 2.3 | 2.1 |
| Aspirin, Pelargonic acid, Butyl benzoate | " | " | 2.4 | 2.5 |
| Aspirin, Pelargonic acid, Ethyl benzoate | " | " | 2.1 | 1.8 |
| Aspirin, Pelargonic acid, Methyl benzoate | " | " | 2.3 | 2.6 |
| Aspirin, Pelargonic acid, Cyclohexanone | " | " | 2.1 | 1.7 |
| Aspirin, Pelargonic acid, Ethylene carbonate | " | " | 2.3 | 2.0 |
| Aspirin, Decanoic acid, Methyl salicylate | " | " | 2.1 | 2.0 |
| Aspirin, Decanoic acid, Cyclohexanone | " | " | 1.7 | 1.6 |
| Aspirin, Decanoic acid, Ethylene carbonate | " | " | 1.5 | 1.7 |
| Aspirin, Decanoic acid, Propylene carbonate | " | " | 1.8 | 1.5 |

TABLE 2-continued

Effective Extractive Distillation Agents

| Compounds | Ratios | | Relative Volatilities | |
|---|---|---|---|---|
| Aspirin, Neodecanoic acid, Methyl salicylate | " | " | 2.3 | 2.8 |
| Aspirin, Neodecanoic acid, Cyclohexanone | " | " | 1.7 | 1.7 |
| Aspirin, Neodecanoic acid, Ethylene carbonate | " | " | 1.6 | 1.8 |
| Aspirin, Neodecanoic acid, Propylene carbonate | " | " | 1.5 | 1.7 |
| Aspirin, Itaconic acid, Ethyl benzoate | " | " | 1.8 | 1.7 |
| Aspirin, Itaconic acid, Methyl salicylate | " | " | 1.9 | 1.9 |
| Aspirin, Dipropylene glycol dibenzoate, Methyl salicylate | " | " | 2.5 | 2.3 |

TABLE 3

Data From Run Made In Rectification Column

| Agent | Column | Time, hrs. | Weight % Water | Weight % Formic acid | Weight % Acetic acid | Relative Volatility |
|---|---|---|---|---|---|---|
| None | Overhead | 0.5 | 40.5 | 29.5 | 30 | |
|  | Bottoms |  | 28 | 24 | 48 | 1.165 |
| " | Overhead | 1 | 39.5 | 30 | 30.5 | |
|  | Bottoms |  | 27 | 25 | 48 | 1.15 |
| 50% Aspirin, | Overhead | 0.5 | 75 | 13 | 12 | |
| 50% Heptanoic acid | Bottoms |  | 12 | 15 | 73 | 1.45 |
| 50% Aspirin | Overhead | 1 | 77 | 18 | 5 | |
| 50% Heptanoic acid | Bottoms |  | 11 | 14 | 75 | 1.93 |
| 50% Aspirin | Overhead | 1.5 | 78 | 18 | 4 | |
| 50% Heptanoic acid | Bottoms |  | 10 | 14 | 76 | 2.03 |

The charge was 40% water, 32% formic acid and 28% acetic acid and after one hour of operation in the 4.5 theoretical plate column to establish equilibrium, aspirin - heptanoic acid mixture at 95%C. and 20 ml/min. was pumped in. The rectification was continued with sampling after one-half hour, one hour and 1.5 hours. The analysis is shown in Table 3 and after 1.5 hours was 78% water, 18% formic acid and 4% acetic acid in the overhead and 10% water, 14% formic acid and 756% acetic acid in the bottoms which gives a relative volatility of 2.03 of formic acid to acetic acid. This indicates that the formic acid - water maximum azeotrope has been negated and separation accomplished. Table 3 shows that with no extractive agent, after one hour, the overhead analysis was 39.5% water, 30% formic acid and 30.5% acetic acid and the bottoms analysis was 27% water, 25% formic acid, 48% acetic acid, which gives a relative volatility of 1.15.

THE USEFULNESS OF THE INVENTION

The usefulness or utility of this invention can be demonstrated by referring to the data presented in Tables 1, 2 and 3. All of the successful extractive agents show that formic acid can be separated from acetic acid by means of distillation in a rectification column and that the ease of separation as measured by relative volatility is considerable. Without these extractive distillation agents, only slight improvement will occur in a rectification column. The data also show that the most attractive agents will operate at a boilup rate low enough to make this a useful and efficient method of recovering high purity formic acid from any mixture with acetic acid and water. The stability of the compounds used and the boiling point difference is such that complete recovery and recycle is obtainable by a simple distillation and the amount required for make-up is small.

WORKING EXAMPLES

Example 1

Twenty-five grams of aqueous formic acid and 25 grams of acetic acid were charged to an Othmer type vapor-liquid equilibrium still and refluxed for 12 hours. Analysis by gas chromatography gave a vapor composition of 40.4% water, 31.9% formic acid and 27.7% acetic acid; a liquid composition of 38.8% water, 30.6% formic acid and 30.6% acetic acid. This indicates a relative volatility of formic acid to acetic acid of 1.15.

Example 2

Eighty grams of water - formic acid - acetic acid mixtures, 25 grams of aspirin and 25 grams of hexanoic acid were charged to the vapor-liquid equilibrium still and refluxed for 13 hours. Analysis indicated a vapor composition of 7% water, 24% formic acid and 81% acetic acid; a liquid composition of 13.4% water, 10.3% formic acid and 76.3% acetic acid which is a relative volatility of 2.6. Five grams of aspirin and five grams of hexanoic acid were added and refluxing continued for another 11 hours. Analysis indicated a vapor composition of 51% water, 19.2% forming acid and 75.7% acetic acid; a liquid composition of 8.6% water, 8.6% formic acid and 82.8% acetic acid which is a relative volatility of 2.4.

Example 3: Fifty grams of water - formic acid - acetic acid mixture, 17 grams of aspirin, 17 grams of hexanoic acid and 17 grams of isophorone were charged to to the vapor-liquid equilibrium still and refluxed for 15 hours. Analysis indicated a vapor composition of 16.5% water, 14.3% formic acid and 69.2% acetic acid; a liquid composition of 17.4% water, 7.2% formic acid and 75.4% acetic acid which is a relative volatility of 2.1. Three grams each of aspirin, hexanoic acid and isophorone were added and refluxing continued for another ten hours. Analysis indicated a vapor composition of 13.1% water, 11.3% formic acid and 75.6% acetic acid; a liquid composition of 16.7% water, 6.7% formic acid and 76.6% acetic acid which is a relative volatility of 2.3.

Example 4

A glass perforated plate rectification column was calibrated with ethylbenzene and p-xylene which possesses a relative volatility of 1.06 and found to have 4.5 theoretical plates. A solution comprising 250 grams of a mixture containing 40% water, 32% formic acid and 28% acetica acid was placed in the stillpot and heated. After a half hour of refluxing at total reflux, analysis of overhead and bottoms gave a relative volatility was 1.165. (see Table 3). After one hour at total reflux, the relative volatility was 1.15. These data confirm the value obtained in the vapor-liquid equilibrium still reported in Example 1. After one hour of operation with the water - formic acid - acetic acid mixture, an extractive agent consisting of 50% aspirin, 50% heptanoic acid was pumped into the column at a rate of 20 ml/min. The temperature of the extractive agent as it entered the column was 95° C. After establishing the feed rate of the extractive agent, the heat input to the water - formic acid - acetic acid mixture in the stillpot was adjusted to give a total reflux rate of 10-20 ml/min. After a half hour of operation, the overhead and bottoms samples of approximately two ml. were collected and analysed by gas chromatography. The overhead analysis was 75% water, 13% formic acid and 12% acetic acid and the bottoms analysis was 12% water, 15% formic acid and 73% acetic acid. Using these compositions in the Fenske equation with the theoretical plates in the column being 4.5, gave an average relative volatility of formic acid to acetic acid of 1.45 for each theoretical plate. After one hour of total operating time, the overhead and bottoms were again sampled and analysed. The overhead was 77% water, 18% formic acid and 5% acetic acid and the bottoms was 11% water, 14% formic acid and 75% acetic acid. This gave an average relative volatility of 1.93 for each theoretical plate. After 1.5 hours of total operating time, the overhead and bottoms were again sampled and analysed. The overhead composition was 78% water, 18% formic acid and 4% acetic acid; the bottoms was 10% water, 14% formic acid and 76% acetic acid. This gave an average relative volatility of 2.03 for each theoretical plate. This agrees with the value obtained with the vapor-liquid equilibrium still and reported in Table 2. It also shows that it takes about 1.5 hours for the column to attain equilibrium conditions.

I claim:

1. A method for recovering formic acid from a mixture comprising formic acid and acetic acid which comprises distilling a mixture of formic acid and acetic acid in a rectification column in the presence of about one part of extractive agent per part of formic acid - acetic acid mixture, recovering the formic acid as overhead product and obtaining the acetic acid and the extractive agent from the stillpot, the extractive agent comprises acetyl salicylic acid and at least one material selected from the group consisting of amyl acetate, butyl benzoate, 2-hydroxyacetophenone, 4-hydroxyacetophenone, methyl amyl acetate, ethyl benzoate, dipropylene glycol dibenzoate, cyclohexanone, 2-heptanone, diisobutyl ketone, isophorone, ethylene carbonate and propylene carbonate. Action on the merits of this amendment is solicated.

2. The method of claim 1 in which the formic acid - acetic acid mixture contains water.

* * * * *